United States Patent
Sharpless

(10) Patent No.: US 8,807,833 B2
(45) Date of Patent: Aug. 19, 2014

(54) CONTROLLED GANTRY IMBALANCE

(75) Inventor: Ronald B. Sharpless, Cleveland, OH (US)

(73) Assignee: Koninklijke Philips N.V., Eindhoven (NL)

( * ) Notice: Subject to any disclaimer, the term of this patent is extended or adjusted under 35 U.S.C. 154(b) by 398 days.

(21) Appl. No.: 13/125,984

(22) PCT Filed: Oct. 29, 2009

(86) PCT No.: PCT/IB2009/054814
§ 371 (c)(1),
(2), (4) Date: Apr. 26, 2011

(87) PCT Pub. No.: WO2010/052623
PCT Pub. Date: May 14, 2010

(65) Prior Publication Data
US 2011/0200176 A1    Aug. 18, 2011

Related U.S. Application Data

(60) Provisional application No. 61/111,345, filed on Nov. 5, 2008.

(51) Int. Cl.
*H05G 1/02*    (2006.01)
*G01M 1/36*    (2006.01)
*A61B 6/03*    (2006.01)
*A61B 6/00*    (2006.01)
*A61B 6/02*    (2006.01)

(52) U.S. Cl.
CPC ........... *G01M 1/36* (2013.01); *A61B 6/4028* (2013.01); *A61B 6/035* (2013.01); *A61B 6/027* (2013.01)
USPC ............................ 378/197; 378/4

(58) Field of Classification Search
USPC ...................... 378/4–20, 193–198
See application file for complete search history.

(56) References Cited

U.S. PATENT DOCUMENTS

| 4,093,862 A | 6/1978 | Brandt et al. |
| 4,750,195 A * | 6/1988 | Takahashi ............... 378/15 |
| 6,580,777 B1 | 6/2003 | Ueki et al. |

(Continued)

FOREIGN PATENT DOCUMENTS

| WO | 0209585 A1 | 2/2002 |
| WO | 2008047308 A1 | 4/2008 |

OTHER PUBLICATIONS

Bender, M., et al.; An Experimental Method for Obtaining the Transfer Function of a Rate Gyro; 1957; IRE Transactions on Instrumentation; I-10(1)35-42.

(Continued)

*Primary Examiner* — Hoon Song

(57) ABSTRACT

An imaging system includes a stationary frame (104) and a pivotable frame (106) that is pivotably attached to the stationary frame (104) and configured to pivot about a transverse axis (108). A rotating frame (110) is rotatably supported by the pivotable portion (106) and configured to rotate about a longitudinal axis (114) around an examination region (112) and a rotating frame balancer (118) selectively introduces a rotating frame mass imbalance. A radiation source (116) is affixed to the rotating frame (110) and emits radiation from a focal spot, wherein the radiation traverses the examination region (112). A detector array (128) detects the radiation that traverses the examination region (112) and generates a signal indicative thereof.

20 Claims, 7 Drawing Sheets

(56) References Cited

U.S. PATENT DOCUMENTS

| | | |
|---|---|---|
| 2002/0168044 A1 | 11/2002 | Tybinkowski et al. |
| 2004/0170254 A1 | 9/2004 | Gregerson et al. |
| 2005/0013403 A1* | 1/2005 | Reznicek et al. ............... 378/15 |
| 2005/0199059 A1 | 9/2005 | Danz et al. |
| 2007/0041488 A1* | 2/2007 | Hoheisel et al. .................. 378/4 |
| 2007/0183557 A1 | 8/2007 | Manzke et al. |

OTHER PUBLICATIONS

Pack, J. D., et al.; Investigation of saddle trajectories for cardiac CT imaging in cone-beam geometry; 2004; Phys. Med. Biol.; 49:2317-2336.

* cited by examiner

US 8,807,833 B2

CONTROLLED GANTRY IMBALANCE

CROSS REFERENCE TO RELATED APPLICATIONS

This application claims the benefit of U.S. provisional application Ser. No. 61/111,345 filed Nov. 5, 2008, which is incorporated herein by reference.

DESCRIPTION

The following relates to imaging systems and finds particular application with computed tomography (CT) imaging. However, it is also amenable to other medical imaging and non-medical imaging applications.

A computed tomography (CT) scanner generally includes an x-ray tube and a detector array that detects radiation emitted from the x-ray tube. The x-ray tube and the detector array are affixed on a rotor on opposite sides of an examination region. The rotor is rotatably supported by a stationary frame and rotates about a longitudinal axis, around the examination region, thereby rotating the x-ray tube and a detector array around the examination region. A patient support supports an object or subject in the examination region. Weights are selectively placed on the rotor to mass balance the rotor. Generally, the weights are stationarily affixed to the rotor during manufacturing. Unfortunately, when not mass balanced, radial forces acting on the components affixed to the rotor tend to cause the rotor to undesirably wobble as the rotor is rotating. The degree of wobble is based on various factors such as the degree of imbalance, the rotational speed of the rotor, the stiffness of the supporting structure, etc.

As the rotor and hence the x-ray tube rotate around the examination region, the x-ray tube emits radiation, from a focal spot, that traverses the examination region and the object or subject disposed therein and illuminates the detector array. A source collimator is used to collimate the radiation so that a generally cone, fan, or wedge shaped radiation beam traverses the examination region. With cone-beam computed tomography, complete sampling of a volume of interest (VOI) is required to reconstruct the VOI without cone beam artifact. However, conventional cone-beam CT scanning techniques that employ a circular radiation source trajectory around the examination region fail to provide complete sampling. Instead, the resulting data set is incomplete in that the sampling of some portions of the VOI is incomplete.

One approach to obtaining complete sampling when using a circular trajectory with cone-beam CT is to perform circle and line scans, and then combine the scans together. However, this requires multiple scans, which may increase scan time, motion artifact, and patient dose. In an alternative approach, the radiation source follows a saddle trajectory to achieve complete sampling of the VOI. Such a trajectory is described in "Investigation of a saddle trajectory for cardiac CT imaging in cone-beam geometry," Pack et al., Phys. Med. Biol., vol. 49, No. 11 (2004) pp. 2317-2336. Unfortunately, to achieve this trajectory the x-ray tube, the focal spot, and/or the patient must be moved back and forth along the z-axis during the scanning procedure.

Aspects herein address the above-referenced matters and/or others.

According to one aspect, an imaging system includes a stationary frame and a pivotable frame that is pivotably attached to the stationary frame and configured to pivot about a transverse axis. A rotating frame is rotatably supported by the pivotable portion and configured to rotate about a longitudinal axis around an examination region and a rotating frame balancer selectively introduces a rotating frame mass imbalance. A radiation source is affixed to the rotating frame and emits radiation from a focal spot, wherein the radiation traverses the examination region. A detector array detects the radiation that traverses the examination region and generates a signal indicative thereof.

According to another aspect, a method includes selectively creating a rotating frame mass imbalance, wherein the rotating frame is part of an imaging system and supports a radiation source of the imaging system.

According to another aspect, an apparatus that creates a rotating frame mass imbalance includes a bearing configured to be affixed to the rotating frame, a moveable mass configured to be affixed to the bearing, a motor that actuates the bearing, and a controller that actuates the motor to move the bearing, which moves the moveable mass between at least a first position and a second position, wherein the first position corresponds to a first mass imbalance.

The invention may take form in various components and arrangements of components, and in various steps and arrangements of steps. The drawings are only for purposes of illustrating the preferred embodiments and are not to be construed as limiting the invention.

Figure 1:
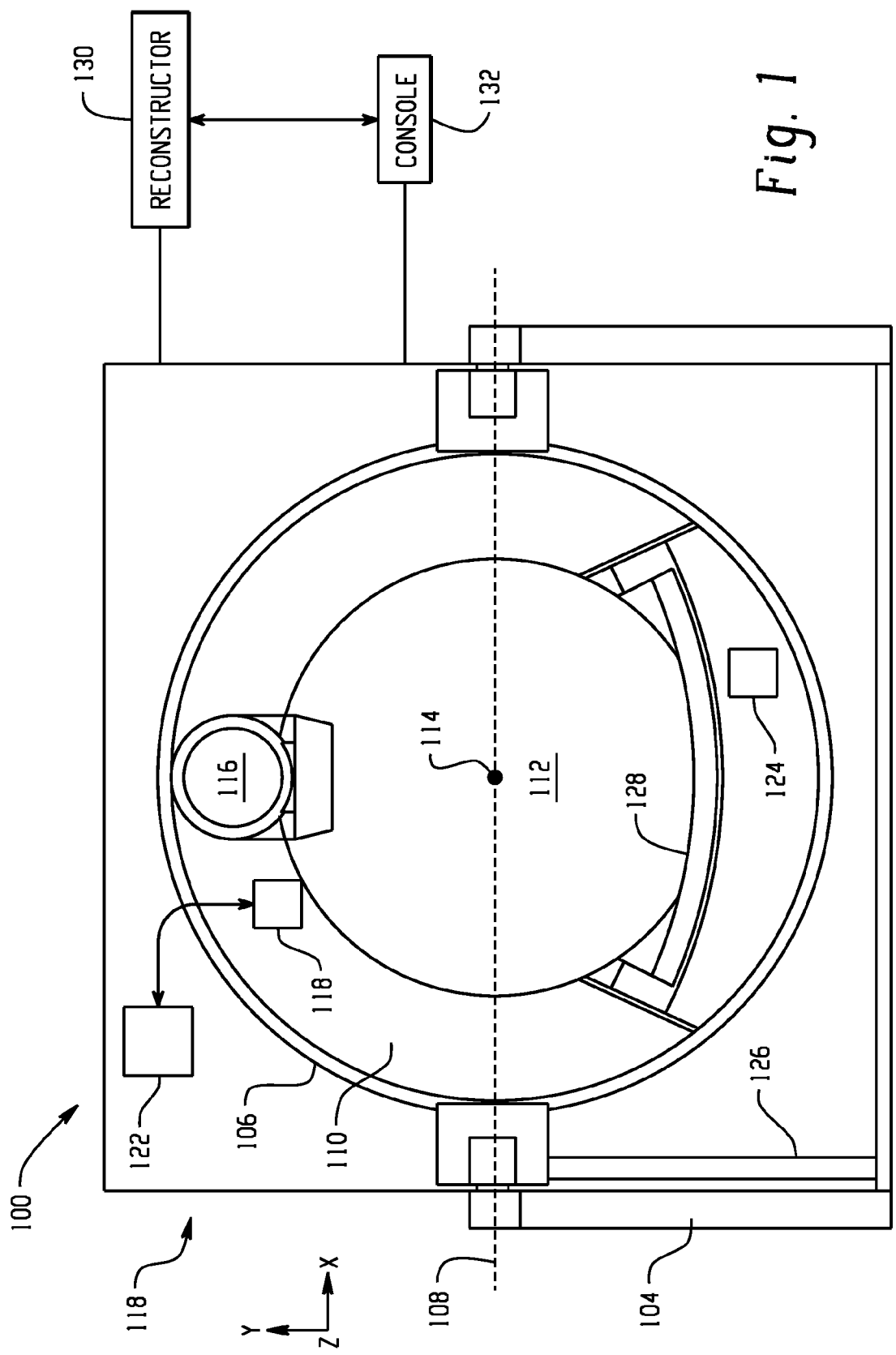
FIG. 1 illustrates an imaging system.

FIG. 1 illustrates a scanner or imaging system 100 that includes a stationary frame 104 and a pivotable or pivoting frame 106, which is pivotably affixed to the stationary frame 104 and configured to pivot about a transverse or x-axis 108.

The imaging system also includes a rotating frame 110, which is rotatably supported by the pivoting frame 106 via a bearing or the like. The rotating frame 110 rotates around an examination region 112 about a longitudinal or z-axis 114 and pivots with the pivoting frame 106 about the pivot 108.

A radiation source 116, such as an x-ray tube, is coupled to and rotates and pivots with the rotating frame 110. As the rotating frame 110 rotates, the radiation source 116 can emit radiation from a focal spot, which follows a scan trajectory. Suitable scan trajectories include, but are not limited to, a saddle, a circular, and an elliptical scan trajectory. A source collimator is used to collimate the radiation so that a generally cone, fan, wedge or otherwise shaped radiation beam traverses the examination region 112.

A rotating frame balancer 118 controllably pivots the rotating frame 110 and, hence, the radiation source 116 about the z-axis 114. In one instance, the rotating frame balancer 118 controllably pivots the rotating frame 110 to move the focal spot through a pre-determined trajectory during a scan, including one of the above-noted trajectories such as a saddle trajectory. As such, when the system 100 is configured for cone-beam scanning, a complete set of data can be obtained for reconstruction purposes.

The rotating frame balancer 118 controllably pivots the rotating frame 110 by introducing a controlled rotating frame mass imbalance. As described in greater detail below, this can be achieved by selectively positioning a moveable mass affixed to the rotating frame 110 along the z-axis 114. In one instance, this leverages rotating frame 110 dynamic imbalances to provide a natural saddle trajectory by exciting this natural motion using a particularly placed mass or imbalance tuned to the mass properties of the pivoting frame 106 and the stiffness of the base 104.

A controller or control component 122 controls the rotating frame balancer 118. Such control may be based on a selected scan protocol and/or otherwise. The control component 122 may be part of rotating frame balancer 118 or a separate component as shown. One or more sensors can be employed to sense the position of the moveable mass, the rotating frame 114, the stationary frame 104, and/or other components of the system. Such sensed information can be used in a feedback loop and/or otherwise, and/or used to facilitate controlling the moveable mass.

The illustrated embodiment also includes a counter mass 124, which can be used to counter the moveable mass, for example, when the moveable mass is at a particular position in order to mass balance the rotating frame 110. The illustrated embodiment also includes a dampener 126 that facilitates the pivoting of the rotating frame 110.

A detector array 128 is affixed to the rotating frame 110 and subtends an angular arc, across from the radiation source 116, opposite the examination region 112. The detector array 128 includes one or more rows of radiation sensitive pixels that extend along a transverse direction. The radiation sensitive pixels detect radiation traversing the examination region 112 and respectively generate a signal indicative thereof.

A reconstructor 130 reconstructs the signals generated by the detector array 128 and generates volumetric image data indicative of the examination region 112.

A patient support (not shown), such as a couch, supports a patient in the examination region 112. The patient support is movable along an x, y and/or z-axis.

A general purpose computing system serves as an operator console 132, which includes input and human readable output devices such as a keyboard and/or mouse and a display and/or printer. Software resident on the computing system controls operation of the system 100, for example, by providing rotating frame imbalance instructions via a user selected scan protocol and/or otherwise.

Figure 2:
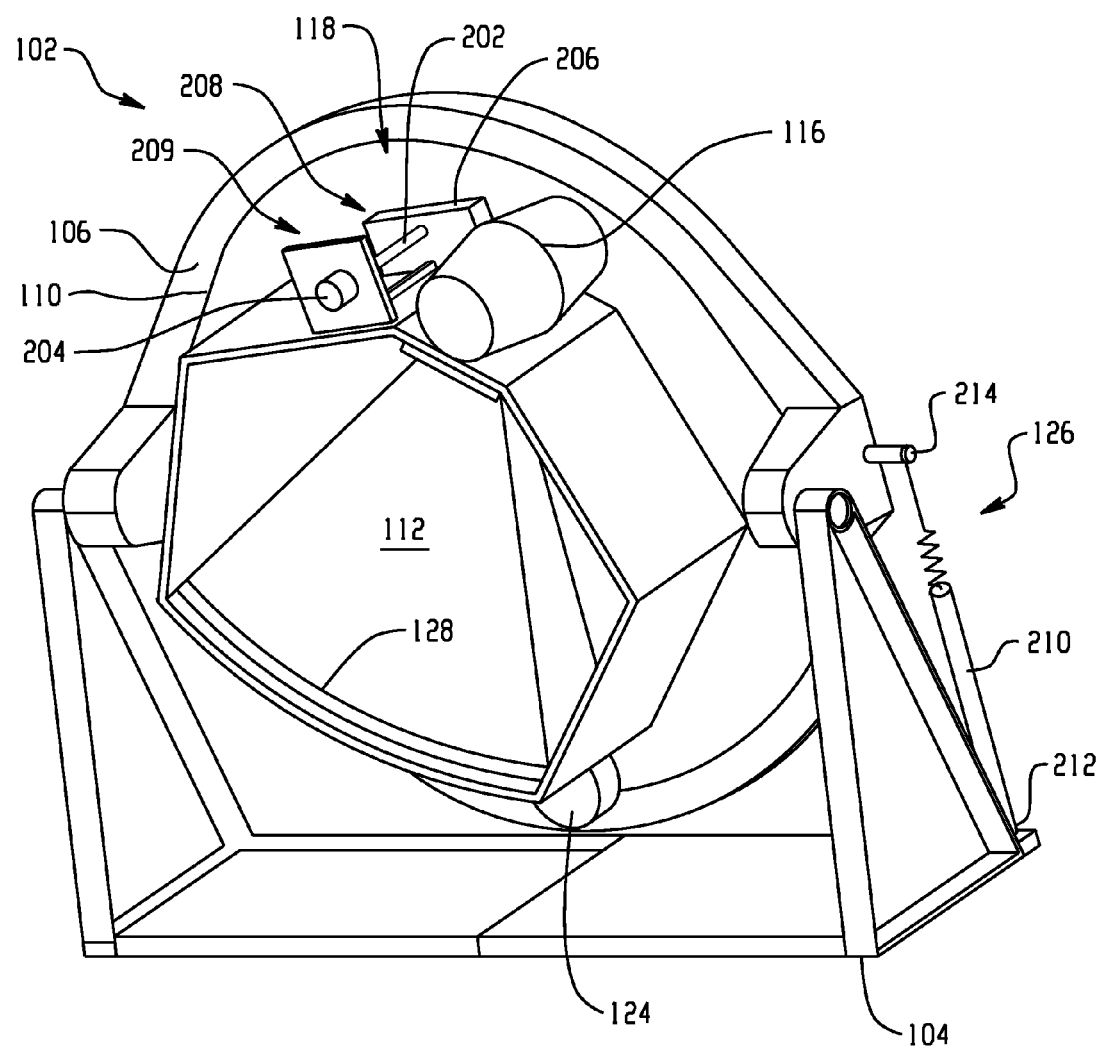
FIG. 2 illustrates an example rotating frame balancer.

FIG. 2 illustrates a non-limiting example of the rotating frame balancer 118. In this example, the rotating frame balancer 118 includes a bearing 202 affixed to the rotating frame 110 and extending therefrom along the z-axis 114, a motor 204 or the like that drives the bearing 202, and a moveable mass 206 affixed to the bearing 202 that translates along the z-axis 114. The bearing 202 can be any type of bearing including, but not limited to, a slide bearing, a lead screw, a ball bearing, etc.

The control component 122 transmits a control signal indicative of a position of the moveable mass 206 along the z-axis 114 to the motor 204. In response, the motor 204 drives the bearing 202, which translates the moveable mass 206 to the position. Suitable positions includes a first position 208 nearer the rotating frame 110, a second position 209, which is relatively farther away from the rotating frame 110, and/or one or more positions therebetween. At least one of the positions balances the mass and at least another of the position introduces a controlled mass imbalance.

In the illustrated embodiment, the counter mass 124 is located on the rotating frame 110 across from the rotating frame balancer 118, on an opposing side of the examination region 112. In the illustrated example, the rotating frame 110 is substantially balanced when the moveable mass 206 is located at the first position and imbalanced when the moveable mass is located at another position. The degree of imbalance is adjustable by selectively translating the moveable mass 206 along the z-axis 114.

The dampener 126 includes a spring mechanism 210, having a first end portion 212 affixed to the base 104 and a second end portion 214 affixed to the pivoting frame 106. The illustrated embodiment includes two dampeners 126. However, it is to be appreciated that other embodiments may include a single or more than two dampeners 126. In addition, other dampeners such as a shock, a piston, etc. can additionally or alternatively be used.

Figure 3:
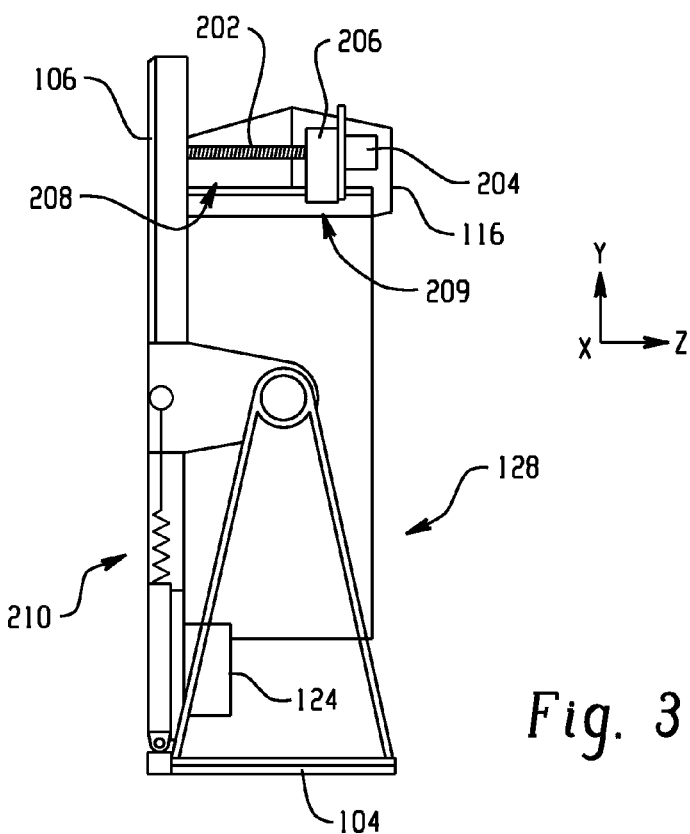
FIGS. 3-6 illustrate an example in which an imbalance is introduced.

FIGS. 3, 4, 5 and 6 illustrate side views of the imaging system 100. FIG. 3 shows a stationary rotating frame 110 with the moveable mass 206 located at about the second position 209. As such, in this example, the moveable mass 206 and the mass 124 are out of plane with respect to each other, and the rotating frame 110 is not balanced, or imbalanced.

Figure 4:
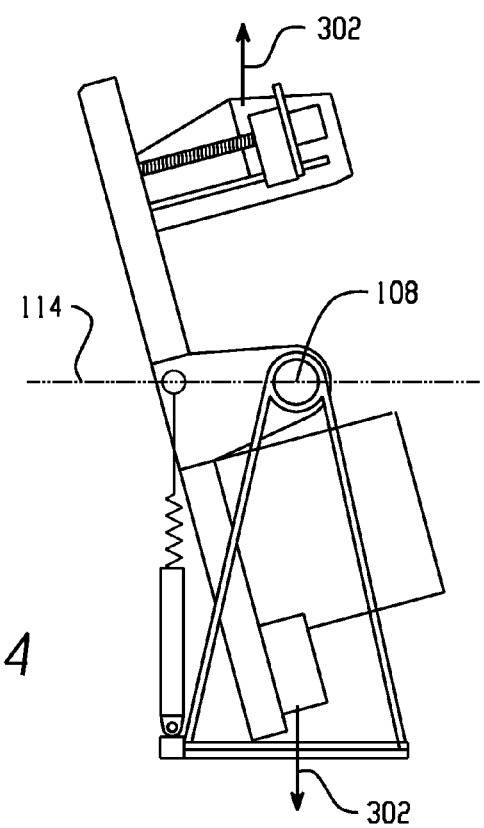
Figure 5:
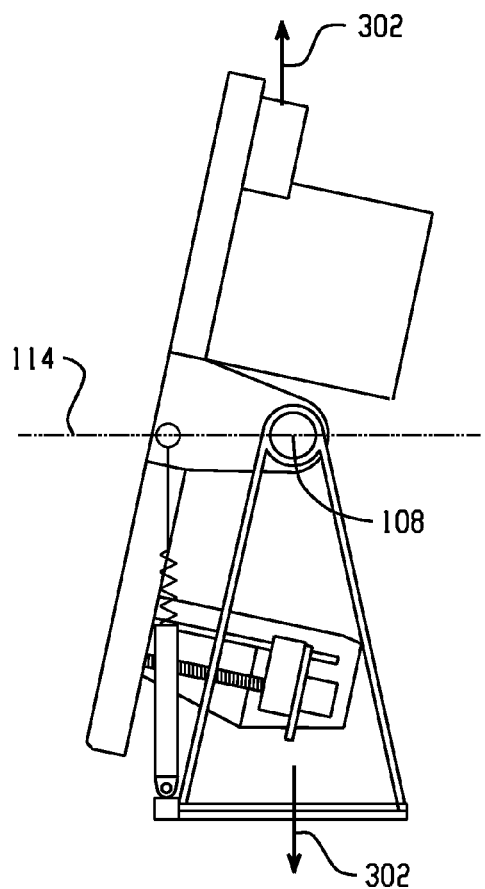
Figure 6:
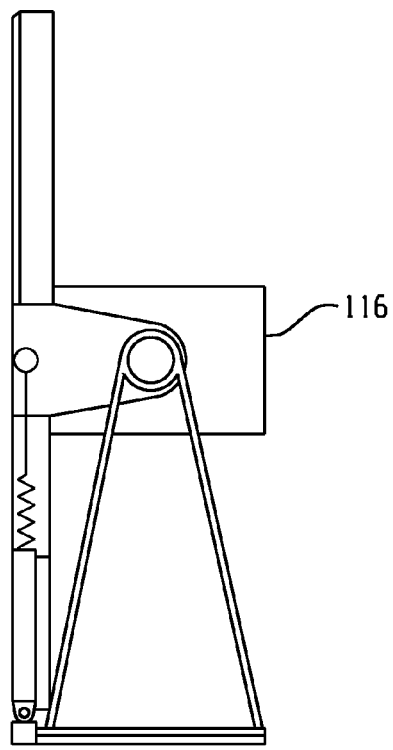

FIGS. 4, 5 and 6 show the pivoting movement of the rotating frame 110 when the moveable mass 206 is at about the second position 209 (as shown in FIG. 3) and the rotating frame 110 is rotating for three different angular positions. FIG. 4 illustrates the rotating frame 110 when the radiation source 116 is located at about the twelve o'clock position or zero degrees. With the masses 206 and 124 being out of plane from each other, radial forces 302 acting on the masses 206 and 124 tend to cause the rotating frame 110 to pivot about the x-axis 108 in a first direction along the z-axis 114.

FIG. 5 illustrates the rotating frame 110 when the radiation source 116 is located at about six o'clock, or 180 degrees opposite twelve o'clock. Again, with the masses 206 and 124 being out of plane from each other, the radial forces 302 acting on the masses 206 and 124 tend to cause the rotating frame 110 to pivot about the x-axis 108. At the six o'clock position, however, the rotating frame 110 pivots in a second direction, which is opposite of the first direction, along the z-axis 114.

FIG. 6 illustrates the rotating frame 110 when the radiation source 116 is located at about the nine o'clock position. As shown, when the radiation source is at this position, the rotating frame 110 does not pivot. In one instance, the stiffness of the supporting frame substantially dampens or cancels the radial forces 302. Likewise, when the radiation source 116 is located at about the three o'clock position, the rotating frame 110 does not pivot.

Figure 7:
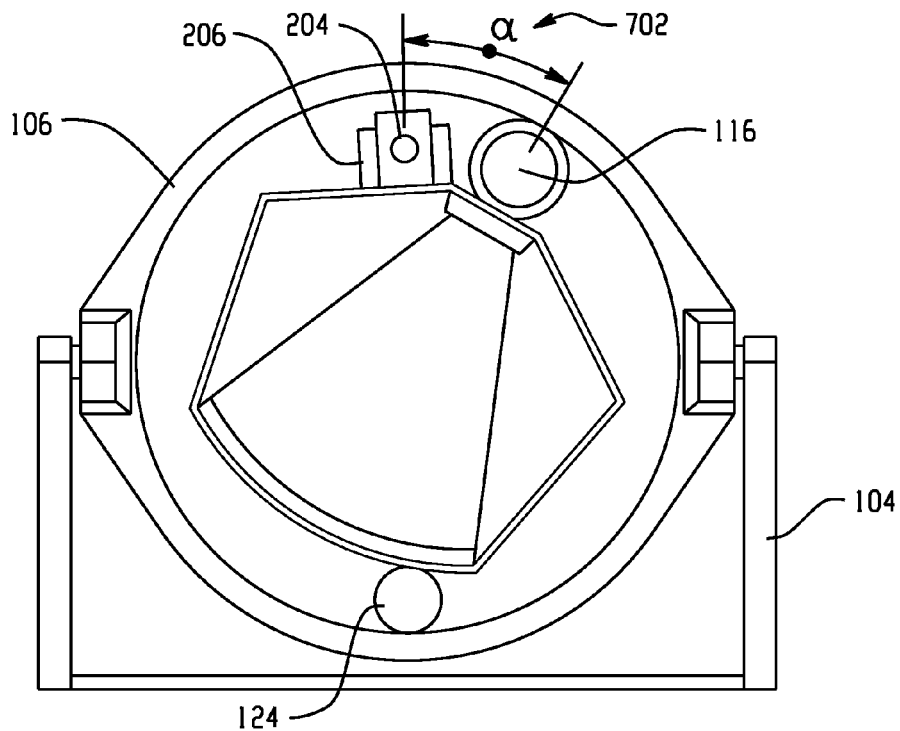
FIG. 7 illustrates relative positions of the rotating frame balancer and the radiation source.

FIG. 7 illustrates a non-limiting example of placement of the masses 206 and 124 on the rotating frame 110. For FIG. 7, assume the rotating frame 110 rotates in a counter clockwise direction. As shown, the mass 206 is angularly offset from the radiation source 116 by an angle $\alpha$ 702 in the direction of rotation and the mass 124 is located across from the mass 206.

In the example of FIGS. 3-6, the value of $\alpha$ 702 is set so that when the radiation source 116 is at the twelve or six o'clock positions (zero/360 or 180 degrees), the focal spot is maximally displaced along the z-axis 114, and when the radiation source 116 is at the three or nine o'clock positions (90 or 270 degrees), the focal spot is at a minimally displaced along the z-axis 114. In other embodiments, the imaging system is otherwise configured so that the maximum displacement occurs at another angular position. In another embodiment, with $\alpha$=90 and no damping, tube and detector displacement is maximized for a particular imbalance.

Factors affecting the angle $\alpha$ 702 include, but are not limited to, the inertia of the pivoting frame 106, the rotational speed at which the rotating frame 110 is configured to be rotated, the stiffness of the rotating frame 110, dampening by the dampeners 126, and/or other factors. The angle $\alpha$ 702 may also be otherwise set such as increased or decreased to change the angular position at which the focal spot is maximally and/or minimally displaced along the z-axis 114. In another instance, the angle α 702 can be modified as a function of the imaging protocol.

Figure 8:
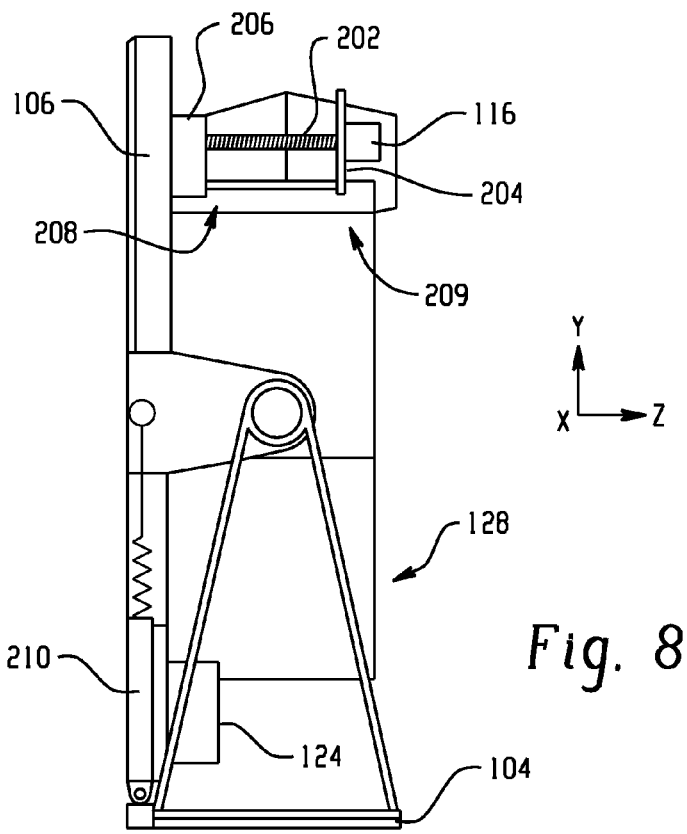
FIG. 8 illustrates an example in which the rotating frame is balanced.

FIG. 8 illustrates the movement of the rotating frame 110 when the moveable mass 206 is at about the first position 208. When the radiation source 116 is located at this position, the rotating frame 110 is substantially balanced through all angular positions as the masses 206 and 124 are positioned in substantially the same plan and the radial forces 302 cancel each other out. As such, the focal spot can be rotated through a circular trajectory.

In another embodiment, at least one of the counter mass 124 and the dampener 126 are omitted.

In another embodiment, an actuator arm is used to push and pull the rotating frame 110 to pivot the rotating frame 110. Such an arm may include one end affixed to the pivoting frame 106 and another end affixed to the base 104. The arm can then controllably extend and contract as the rotating frame 110 rotates to pivot the pivoting frame 106 and hence the rotating frame 110 and the focal spot.

In another embodiment, the moveable mass 206 is alternatively or additionally configured to circumferentially move in order to introduce the imbalance.

Figure 9:
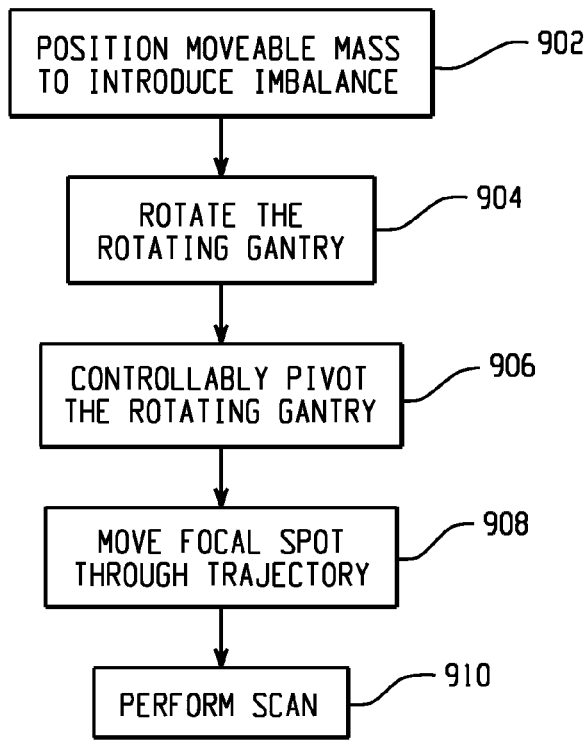
FIGS. 9-11 illustrate example methods.

FIG. 9 illustrates a first method. It is to be appreciated that the following acts may occur in a different order and in other embodiments, more, less and/or different acts can be employed.

At 902, the moveable mass 206 is suitably positioned along at least the z-axis 114 with respect to the rotating frame 110 to controllably introduce a mass imbalance on the rotating frame 110.

At 904, the rotating frame 110 ramps up to a rotational speed in accordance with the selected scan protocol.

At 906, the imbalance causes the rotating frame 110 to controllably pivot about the x-axis 108 while it rotates around the z-axis based.

At 908, the focal spot follows the trajectory created by this movement. As noted above, the trajectory may be a saddle or other trajectory.

At 910, a scan is performed.

Figure 10:
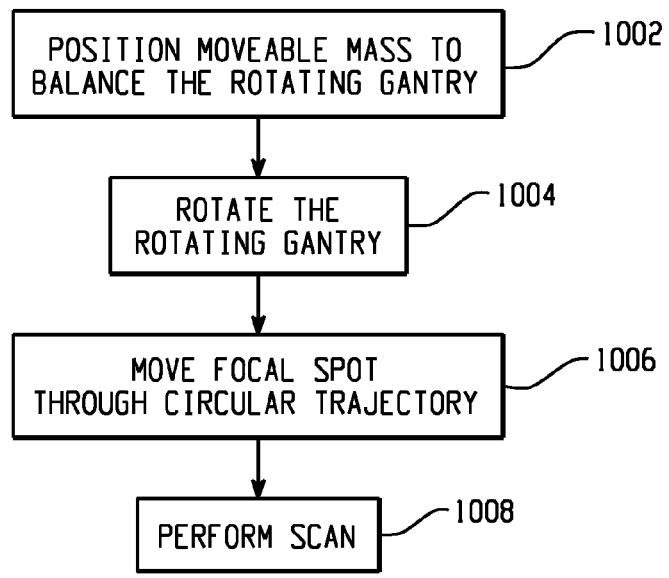

FIG. 10 illustrates another method. Again, it is to be appreciated that the following acts may occur in a different order and in other embodiments, more, less and/or different acts can be employed.

At 1002, the moveable mass 206 is suitably positioned along at least the z-axis 114 with respect to the rotating frame 110 to balance the rotating frame 110.

At 1004, the rotating frame 110 ramps up to speed in accordance with the selected scan protocol.

At 1006, the focal spot follows a circular trajectory as the rotating frame 110 is mass balanced.

At 1008, a scan is performed.

Figure 11:
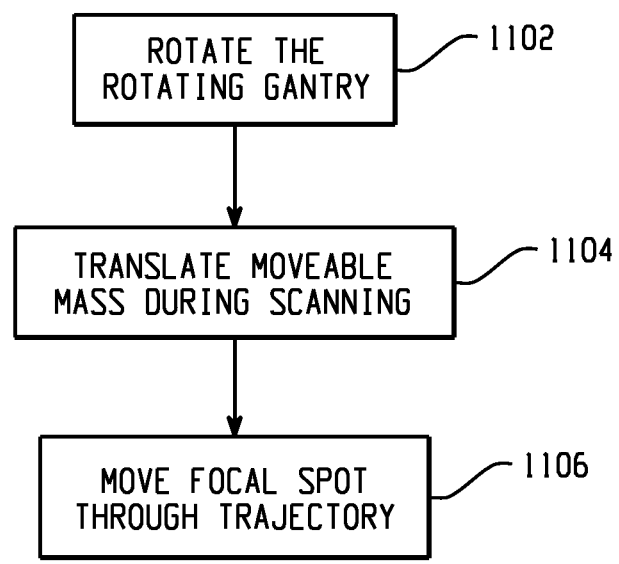

FIG. 11 illustrates another method.

At 1102, the rotating frame 110 ramps up to speed in accordance with the selected scan protocol.

At 1104, the moveable mass 206 dynamically controllably translates to one or more positions along the z-axis 114 during scanning.

At 1106, the focal spot follows the trajectory created by this movement.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

The invention is claimed to be:

1. An imaging system, comprising:
   a stationary frame;
   a pivotable frame that is pivotably attached to the stationary frame and configured to pivot about a transverse axis;
   a rotating frame that is rotatably supported by the pivotable frame and configured to rotate about a longitudinal axis around an examination region;
   a rotating frame balancer configured to selectively introduce a rotating frame mass imbalance during scanning a subject;
   a radiation source that is affixed to the rotating frame and that emits radiation from a focal spot, wherein the radiation traverses the examination region; and
   a detector array that detects the radiation that traverses the examination region and generates a signal indicative thereof.

2. The system of claim 1, wherein the imbalance causes the pivotable frame to pivot back and forth about the transverse axis while the rotating frame rotates around the longitudinal axis.

3. The system of claim 2, wherein the pivoting rotating frame translates the focal spot back and forth along the longitudinal axis.

4. The system of claim 2, wherein the pivoting rotating frame moves the focal spot along a desired scan trajectory.

5. The system of claim 4, wherein the scan trajectory is a saddle trajectory.

6. The system of claim 1, where the rotating frame balancer includes a moveable mass configured to translate along the longitudinal axis.

7. The system of claim 6, wherein the rotating frame balancer further includes:
   a bearing affixed to the rotating frame;
   a motor that actuates the bearing; and
   a controller that control the motor, wherein the moveable mass is affixed to the bearing, and the controller provides a control signal that actuates the motor to move the bearing, thereby moving the moveable mass.

8. The system of claim 7, further including:
   a counter mass located on the rotating frame, across from the rotating frame balancer, opposite the examination region.

9. The system of claim 1, wherein the rotating frame balancer is angularly offset from the radiation source by an angle α.

10. The system of claim 9, wherein the angle α determines at least a maximum displacement of the focal spot along the longitudinal axis.

11. The system of claim 9, wherein the angle α is a function of the imaging protocol.

12. The system of claim 1, further including a dampener that dampens pivoting of the pivotable frame.

13. The system of claim 1, wherein the rotating frame balancer varies the mass imbalance while the rotating frame rotates.

14. A method, comprising selectively creating a rotating frame mass imbalance during scanning a subject based on a focal spot trajectory of interest of the scan, wherein the rotating frame is part of an imaging system and supports a radiation source of the imaging system.

15. The method of claim 14, wherein the mass imbalance defines a focal spot trajectory of a focal spot of the radiation source.

16. The method of claim 14, wherein creating the rotating frame mass imbalance includes selectively moving a mass moveably affixed to the rotating frame along a longitudinal axis.

17. The method of claim 14, wherein the imbalance causes the rotating frame to pivot about a pivot axis.

18. The method of claim 17, wherein pivoting the rotating frame cyclically translates the focal spot back and forth.

19. An apparatus that controllably creates a mass imbalance for a rotating frame of a scanner, the system comprising:
- a bearing configured to be affixed to the rotating frame;
- a moveable mass configured to be affixed to the bearing; and
- a motor that actuates the bearing; and
- a controller that actuates the motor to move the bearing, thereby moving the moveable mass between at least a first position and a second position, wherein the first position corresponds to a first mass imbalance and hence controllably moving an x-ray source affixed to the rotating frame along a longitudinal axis to move the x-ray source through a source trajectory of interest of a scan.

20. The apparatus of claim 19, further including:
- a counter mass located on the rotating frame, across from the rotating frame balancer, opposite an examination region; and
- a dampener that dampens pivoting motion of the rotating frame, wherein the dampener includes a spring mechanism having a first end portion affixed to a base of the scanner and a second end affixed to the rotating frame of the scanner.

* * * * *